(12) United States Patent
Cobianu et al.

(10) Patent No.: US 8,479,560 B2
(45) Date of Patent: Jul. 9, 2013

(54) DIFFERENTIAL RESONANT SENSOR APPARATUS AND METHOD FOR DETECTING RELATIVE HUMIDITY

(75) Inventors: Cornel Cobianu, Bucharest (RO); Bogdan Serban, Bucharest (RO); Mihai N. Mihaila, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 260 days.

(21) Appl. No.: 12/895,410

(22) Filed: Sep. 30, 2010

(65) Prior Publication Data
US 2011/0239759 A1    Oct. 6, 2011

Related U.S. Application Data

(60) Provisional application No. 61/318,857, filed on Mar. 30, 2010.

(51) Int. Cl.
*G01N 7/00* (2006.01)

(52) U.S. Cl.
USPC ...................................................... 73/29.01

(58) Field of Classification Search
USPC ............... 73/29.01, 29.02, 335.01–335.09, 73/29.04–29.05, 24.01, 24.03, 24.04, 24.05, 73/24.06, 1.82, 1.86, 31.05, 31.06
See application file for complete search history.

(56) References Cited

U.S. PATENT DOCUMENTS

| | | | |
|---|---|---|---|
| 3,266,291 A * | 8/1966 | King, Jr. ...................... 73/24.06 |
| 3,561,253 A | 2/1971 | Dorman | |
| 5,571,944 A * | 11/1996 | Pfeifer et al. ................. 73/24.04 |
| 5,852,229 A * | 12/1998 | Josse et al. ................... 73/24.06 |
| 6,167,748 B1 | 1/2001 | Britton, Jr. et al. | |
| 6,197,515 B1 | 3/2001 | Bamdad et al. ................... 435/6 |

(Continued)

FOREIGN PATENT DOCUMENTS
EP    0 072 744 A2    2/1933

OTHER PUBLICATIONS

M. Li, H.X. Tang, M.L. Roukes; Ultra sensitive NEMSbased Cantilevers for Sensing, Scanned Probe and very HighFrequency Applications; vol. 2, Feb. 2007,www.nature.com/naturenanotechnology.
K.L. Ekinci,X.M.H. Huang, M.L. Roukes; Ultrasensitive Nanoelectromechanical Mass Detection; Applied Physics Letters, vol. 84 No. 22, May 31, 2004.

(Continued)

*Primary Examiner* — Daniel Larkin
*Assistant Examiner* — Jamar Ray
(74) *Attorney, Agent, or Firm* — Kermit D. Lopez; Luis M. Ortiz; Tuesday A. Kaasch (57) ABSTRACT

A differential resonant sensor apparatus and method for detecting relative humidity in an ambient air. The apparatus generally includes a sensing loop, a reference loop and a mixer. A hydrophilic sensing layer can be deposited on a sensing resonant beam and a corresponding hydrophobic reference layer can be deposited on a reference resonant beam for detecting water vapor concentration in the ambient air. The hydrophobic reference layer possesses similar viscoelastic properties as the hydrophilic sensing layer with no water absorption properties. A differential reading electronic circuit may be interconnected with each resonant beam for signal processing. The absorbed humidity with respect to the sensing resonant beam changes the mechanical resonance frequency, which can be detected as a change in the electric resonance frequency of the associated electronic circuit.

14 Claims, 8 Drawing Sheets

U.S. PATENT DOCUMENTS

| | | | |
|---|---|---|---|
| 6,306,584 B1 | 10/2001 | Bamdad | 435/6 |
| 6,342,347 B1 | 1/2002 | Bauer | 435/4 |
| 6,378,370 B1 * | 4/2002 | Haskell et al. | 73/579 |
| 6,722,200 B2 | 4/2004 | Roukes et al. | 73/580 |
| 7,134,319 B2 * | 11/2006 | Liu | 73/31.06 |
| 7,181,836 B2 | 2/2007 | Tsakalakos | 29/846 |
| 7,207,206 B2 | 4/2007 | Pinnaduwage et al. | 73/23.2 |
| 7,500,379 B2 * | 3/2009 | Hines | 73/24.06 |
| 2005/0161749 A1 | 7/2005 | Yang et al. | 257/414 |
| 2005/0262943 A1 | 12/2005 | Claydon et al. | |
| 2007/0120252 A1 | 5/2007 | Tsakalakos | 257/734 |
| 2007/0151099 A1 | 7/2007 | Tsakalakos | 29/846 |
| 2007/0255166 A1 | 11/2007 | Carney et al. | 600/561 |
| 2008/0085212 A1 | 4/2008 | Adams et al. | |
| 2008/0245135 A1 | 10/2008 | Aubin et al. | 73/61.49 |
| 2010/0000292 A1 * | 1/2010 | Karabacak et al. | 73/24.01 |

OTHER PUBLICATIONS

Y.T.Yang, C.Callegari, X.L. Feng, K.L. Ekinici, M.L. Roukes; ZeptogramScale Nanomechanical Mass Sensing; Nano Letters, vol. 6 No. 4, Apr. 2006.

F.W. Bell, A. Wixforth, R.H. Blick; P2-21: Broadband Acoustical Tuning of Nano-Electromechanical Sensors; IEEE 2002.

A. Husain, J. Hone, H.W. Ch.Postma, X.M.H. Huang, T. Drake, M. Barbic, A. Scherer, M.L. Roukes; Nanowirebased Very-High-Frequency Electromechanical Resonator; Applied Physics Letters, Vol. 83 No.6, Aug. 11, 2003.

EP Search Report dated Jun. 29, 2011 for EP Application 11156697.2.

* cited by examiner

DIFFERENTIAL RESONANT SENSOR APPARATUS AND METHOD FOR DETECTING RELATIVE HUMIDITY

CROSS-REFERENCE TO PROVISIONAL APPLICATION

This non-provisional patent application claims the benefit under 35 U.S.C. §119(e) to U.S. Provisional Patent Application Ser. No. 61/318,857 filed on Mar. 30, 2010, entitled "Differential Resonant Sensor Apparatus and Method for Detecting Relative Humidity," which is hereby incorporated by reference in its entirety.

TECHNICAL FIELD

Embodiments are generally related to sensing devices and techniques. Embodiments are also related to differential resonant sensors. Embodiments are additionally related to methods for detecting relative humidity in ambient air.

BACKGROUND OF THE INVENTION

Numerous applications require controlling a defined environment's air quality characteristics, including providing an environment having a narrow range of relative humidity (RH) and/or preventing the creation of extreme relative humidity conditions. Indoor air quality can be impacted by air contaminants such as humidity, volatile organic compounds (VOC), semi volatile organic compounds (SVOC), and particulate material. Hence, it is desirable to control not only the air quality, but also relative humidity in order to provide a good quality of indoor air at a low electric energy consumption.

Most prior art relative humidity sensors are capacitive sensors that include a thermosetting polymer as a dielectric layer. The thermosetting polymer possesses a high capability of water vapor absorption. The water vapors can be adsorbed and absorbed by the thermosetting polymeric dielectric and the dielectric constant of the polymer can be increased, which can further increase the capacitance value. Such capacitive detection is effective for integrated humidity sensors, where the parasitic capacitances of wire bonding the sensor and its associated electronics are eliminated.

Problems associated with such capacitive sensors includes cost, a lack of long term performance stability and poor drift behavior due to poor baseline stability (i.e., recovery of the sensor signal to the same response level in the absence of the humidity to be detected). Other problems include aging of the sensing material, which may exhibit or contribute to the baseline drift and poor accuracy. Furthermore, prior art differential resonant sensing approaches for measuring different gases and bio-chemicals often include a coated sensing layer and an uncoated reference surface. The coated sensing layer can sense variants, while the uncoated reference layer can be employed to eliminate common disturbances. Such an uncoated reference layer may not be efficient in removing all common mode signals.

Based on the foregoing, it is believed that a need exists for an improved differential resonant sensor apparatus and method for detecting relative humidity in ambient air. A need also exists for fabricating the differential resonant sensor apparatus in association with a coated reference layer for eliminating the effects of baseline drift, as described in greater detail herein.

BRIEF SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved relative humidity detection apparatus and method.

It is another aspect of the disclosed embodiments to provide for an improved differential resonant sensor apparatus and method for detecting relative humidity in ambient air.

It is a further aspect of the disclosed embodiments to provide for an improved method for fabricating a differential resonant apparatus in association with a coated reference layer for eliminating the effects of baseline drift.

The aforementioned aspects and other objectives and advantages can now be achieved as described herein. A differential resonant sensor apparatus and method for detecting relative humidity in an ambient air is disclosed herein. The apparatus generally includes a sensing loop, a reference loop and a mixer. A hydrophilic sensing layer (e.g., sulfonated carbon nanotube) can be deposited on a sensing resonant beam and a corresponding hydrophobic reference layer (e.g., carbon nanotube) can be deposited on a reference resonant beam for detecting water vapor concentration in the ambient air by a differential principle. The hydrophobic reference layer possesses similar visco-elastic properties (e.g., temperature, humidity and aging) as the hydrophilic sensing layer with no water absorption properties. A differential reading electronic circuit may be interconnected with the output of circuits for signal processing from each resonant beam. The absorbed humidity with respect to the sensing resonant beam changes its mechanical resonance frequency, which can be detected as a change in the electric resonance frequency of its associated electronic circuit. The output of the mixer will provide the difference between the resonance frequency of the sensing resonant beam and the frequency of the reference resonant beam and thus will give a drift free output signal carrying the information about the humidity.

The water vapor concentration can be sensed in addition to the detection of toxic contaminations (e.g., $CO_2$, toxic and combustion gases, etc) in the ambient air. The common mode signal of the sensing and the reference resonators due to temperature variation, aging of the resonant beams and the sensing and reference layers can be rejected utilizing a differential approach with respect to the sensor and the electronic circuit. The electronic circuits associated with the sensing loop and the reference loop possess identical functional operations, with a similar noise and aging response. The sensor apparatus may be fully integrated on a single substrate together with the differential interrogation electronics.

The apparatus may be fabricated by initially processing a wafer (e.g., complementary metal-oxide-semiconductor (CMOS) silicon on insulator (SOD) to include elements associated with the sensing loop, the reference loop and the electronic circuit for electronic signal processing. A suspended beam can then be released in order to form the resonant beam. The functionalization of the sensing resonant beam and the reference resonant beam may be performed via a process compatible with, for example, a CMOS SOI technology. The liquid phase of hydrophilic sensing layer and the hydrophobic reference layer can be deposited on the corresponding beam by a direct printing approach, compatible with the width of the beam. The disclosed differential resonant sensor apparatus containing on-chip sensing and reference layers can therefore provide a genuine relative humidity sensing application, in association with the electronic circuit.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

Figure 1:
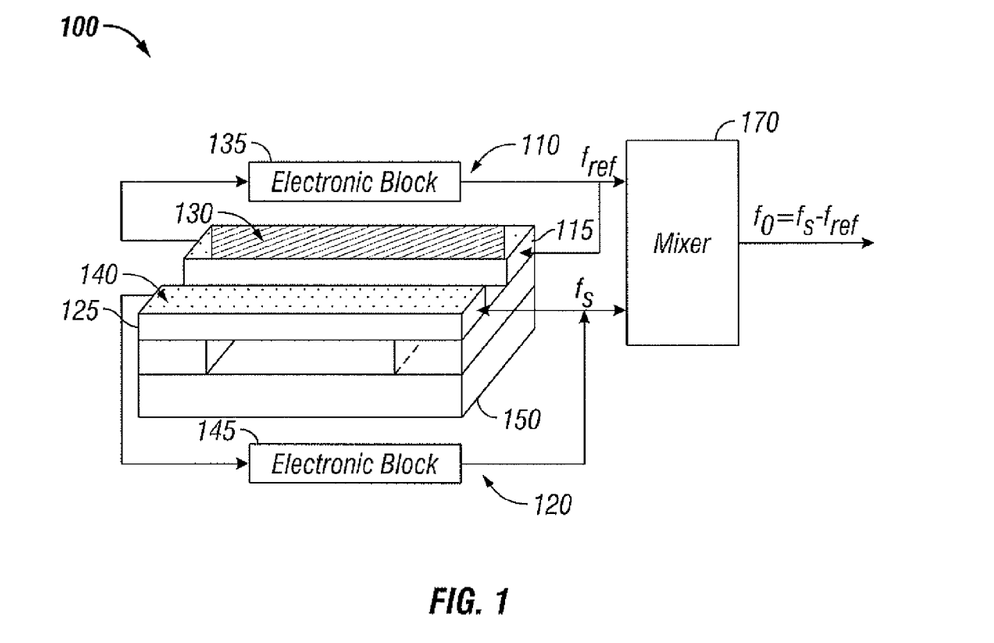
FIG. 1 illustrates a perspective view of a differential resonant sensor apparatus, in accordance with the disclosed embodiments.

FIG. 1 illustrates a perspective view of a differential resonant sensor apparatus 100, in accordance with the disclosed embodiments. The differential resonant sensor apparatus 100 can be employed to detect relative humidity (RH) in an ambient air utilizing MEMS-NEMS silicon technology. The differential resonant sensor apparatus 100 can be integrated on a chip 150 of a substrate wafer (e.g., silicon wafer, not shown) together with the differential interrogation electronic blocks 135 and 145. The sensor apparatus 100 includes a sensing loop 120, a reference loop 110 and a mixer 170 located at the output of the electronic blocks 135 and 145 for resonance frequency measurement. The sensing loop 120 further includes a sensing resonant beam 125 and the reference loop 110 includes a reference resonant beam 115.

A hydrophilic sensing layer 140 can be deposited onto the surface of the sensing resonant beam 125 in order to sense relative humidity (RH) in the ambient air. Similarly, a hydrophobic reference layer 130 can be deposited on the reference resonant beam 115 with no sensing properties, but, which possesses similar visco-elastic properties as the sensing layer. The sensing resonant beam 125 can be functionalized to measure a resonance frequency shift, which includes data regarding the temperature, humidity variations, gas atoms adsorption-desorption fluctuations on the resonator beam 125 and aging of the sensing layer 140. Similarly, the reference resonant beam 115 may provide the resonance frequency shift, which includes data regarding temperature, atom adsorption-desorption fluctuations on the resonator 115, the aging of the reference layer 130.

The hydrophilic sensing layer 140 associated with the sensing resonant beam 125 can absorb water vapor and sense the concentration of humidity in ambient air. The hydrophobic reference layer 130 associated with the reference resonant beam 115 does not absorb the water vapor and does not sense the concentration of humidity. The absorbed humidity with respect to the sensing resonant beam 125 changes the mechanical resonance frequency, which can be detected as a change in the electric resonance frequency of the associated electronic circuit. The common mode signal of the sensing and the reference loops 120 and 110, respectively, due to temperature variation, humidity adsorption, aging of the resonant beams 115 and 125 and the sensing and reference layers 140 and 130, respectively, may be rejected utilizing a differential approach with respect to the sensor 100 and the electronic circuit. The electronic blocks 135 and 145 associated with the sensing loop 120 and the reference loop 110, respectively, possess identical functional operations, with a similar noise and aging response, with respect to the humidity detection.

Figure 2:
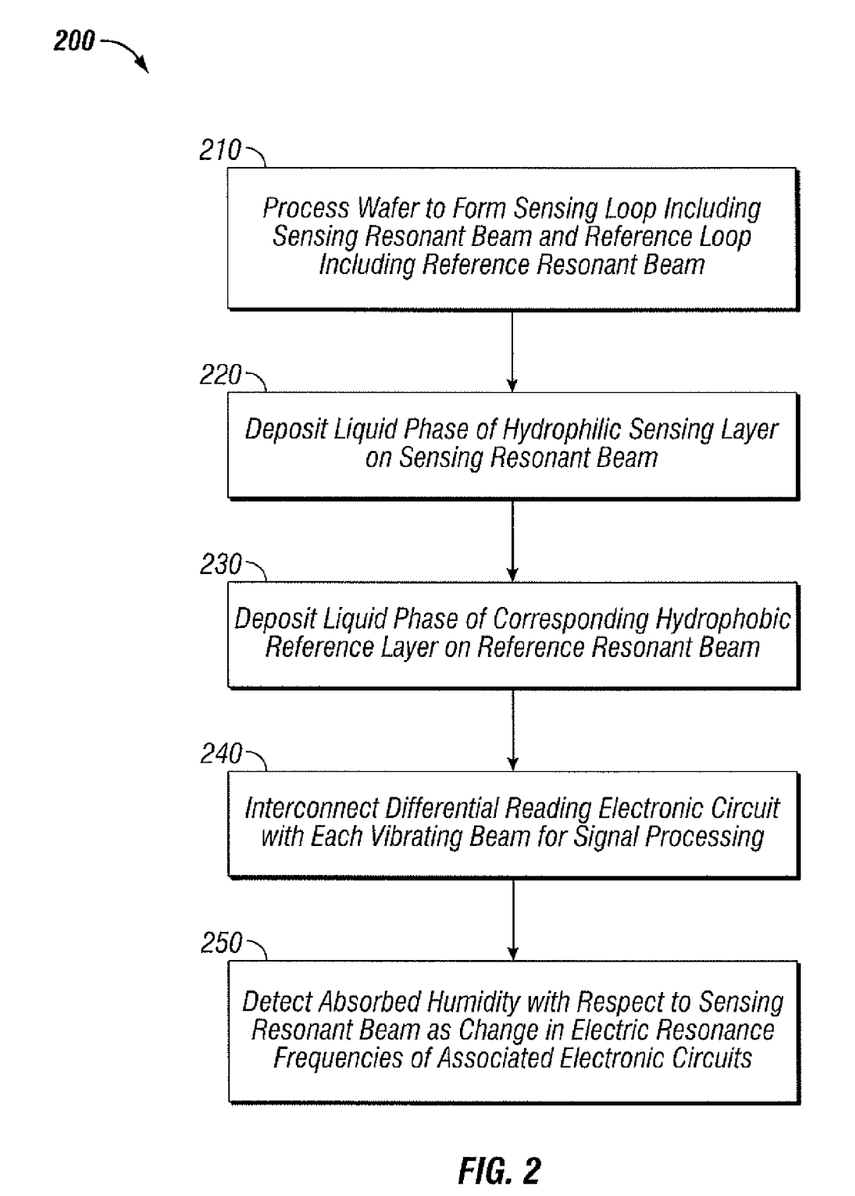
FIG. 2 illustrates a high level flow chart of operation illustrating logical operation steps of a method for detecting relative humidity in ambient air, in accordance with the disclosed embodiments.

FIG. 2 illustrates a high level flow chart of operation illustrating logical operation steps of a method 200 for detecting relative humidity in ambient air, in accordance with the disclosed embodiments. Note that in FIGS. 1-13, identical or similar blocks are generally indicated by identical reference numerals. As part of a wafer not shown here, the chip 150, can be processed to form the sensing loop 120 including the sensing resonant beam 125 and the reference loop 110 including the reference resonant beam 115, as indicated at block 210. The apparatus 100 can be fabricated by initially processing the wafer (e.g., complementary metal-oxide-semiconductor (CMOS) silicon on insulator (SOD) to include elements associated with the sensing loop 120, the reference loop 110 and the electronic blocks 135 and 145.

A suspended beam can be then released in order to form the resonant beams 125 and 115. The functionalization of the sensing resonant beam 125 and the reference resonant beam 115 may be performed via a process compatible with, for example, a CMOS SOI technology. The complementary metal-oxide-semiconductor is a technology for configuring integrated circuits and the silicon on insulator technology refers to the use of a layered silicon-insulator-silicon substrate in place of conventional silicon substrates in semiconductor manufacturing, to reduce parasitic device capacitance and thereby improving performance. The sensor apparatus 100 may be fully integrated on a single substrate together with the differential interrogation electronics.

A liquid phase of the hydrophilic sensing layer 140 can be deposited on the sensing resonant beam 125, as illustrated at block 220. A liquid phase of the corresponding hydrophobic reference layer 130 can be deposited on the reference resonant beam 115 for detecting water vapor concentration in the ambient air, as depicted at block 230. The hydrophobic reference layer 130 possesses similar visco-elastic properties (e.g., temperature, humidity and aging) as the hydrophilic sensing layer with no water absorption properties. The sensing layer 140 and the reference layer 130 can be dried and thermally consolidated in order to obtain a functionalized thin solid film. The reading electronic circuits 135 and 145 may be interconnected with each resonant beam for signal processing, providing the electronic resonance frequencies of those electronic circuits, as illustrated at block 240. Note that each of the reading electronic circuit 135 and 145 are preferably configured to contain or include an actuation circuit and a detection circuit, wherein the actuation circuit includes components for driving and sustaining a beam at its mechanical resonance frequency, while the detection circuit is configured to measure an electronic resonance frequency that is equal to the mechanical resonance frequency of the vibrating beam. A differential reading circuit, containing a mixer, for example, can be employed at the output of the two electronic blocks, 135 and 145. The absorbed humidity with respect to the sensing resonant beam 125 changes its mechanical resonance frequency, which can be detected as a change in the electric resonance frequency of the associated electronic circuit 120, and this further alters the difference between the electronic resonance frequency of sensing loop 120 and the electronic resonance frequency of the reference loop 110, which can be revealed at the output of the mixer 170, as described above and indicated at block 250.

Figure 3:
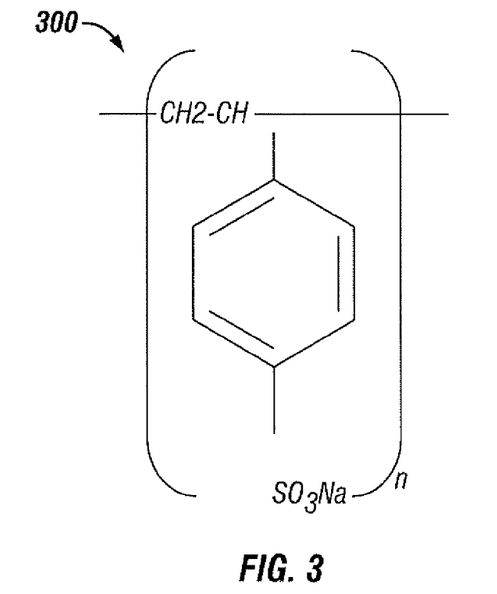
FIGS. 3-4 illustrate an exemplary sequence of chemical reactions for forming a hydrophilic sensing layer and a corresponding hydrophobic reference layer, in accordance with the disclosed embodiments.
Figure 4:
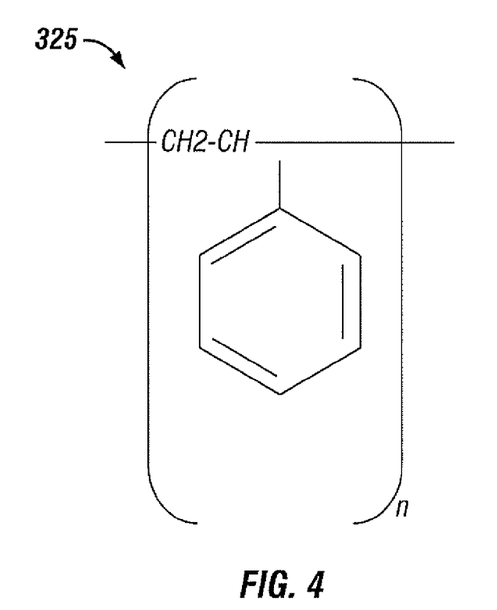

FIGS. 3-4 illustrate an exemplary sequence of chemical reactions for forming the hydrophilic sensing layer 140 and the corresponding hydrophobic reference layer 130 with respect to the resonant beams 125 and 115, respectively, in accordance with the disclosed embodiments. The sensing layer 140 can be made from sulfonated polystyrene 300 and the corresponding reference layer 130 can be made from polystyrene 325. In order to obtain the liquid phase of the sensing layer 140, polystyrene can be sulfonated in the presence of sulphuric acid that results in the formation of polystyrene sulfonic acid. The polystyrene sulfonic acid can be further neutralized in the presence of sodium hydroxide in order to form the poly (sodium p-styrene) sulfonate. The poly (sodium p-styrene) sulfonate can be dissolved in toluene, and the liquid solution can be employed in the formation of the sensing layer 140. Similarly, the liquid phase of the polystyrene 300 can be obtained by dissolving the commercial material in toluene and obtaining the right value of the solution viscosity as required and the necessary final thickness of the reference layer 130.

Figure 5:
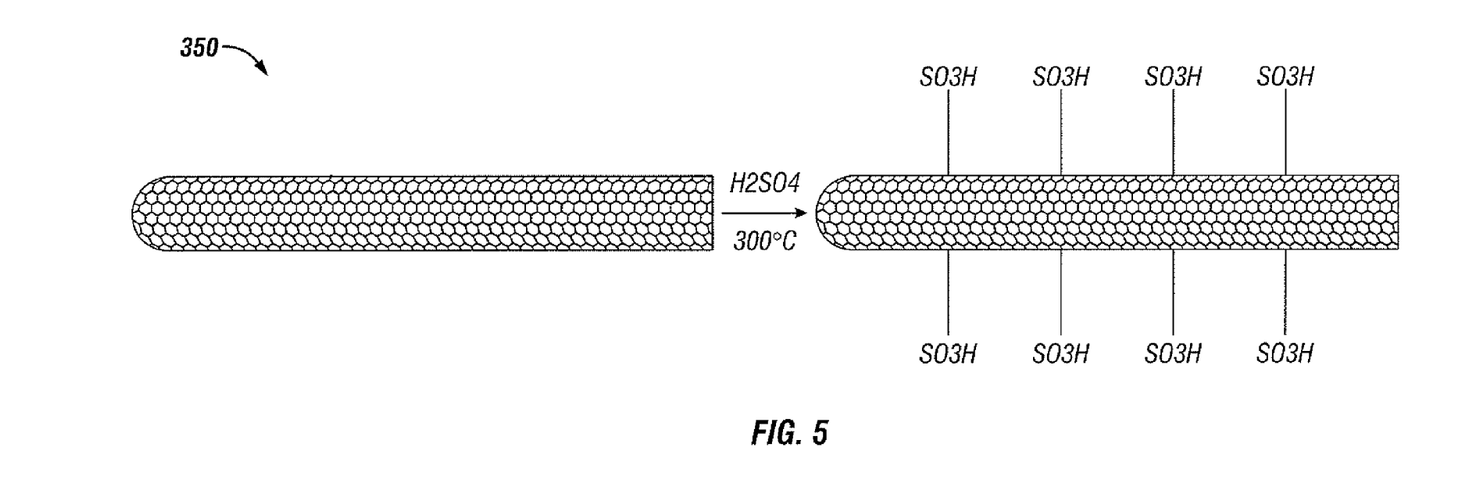
FIGS. 5-6 illustrate an exemplary sequence of chemical reactions for forming the hydrophilic sensing layer and the corresponding hydrophobic reference, in accordance with the disclosed embodiments.
Figure 6:
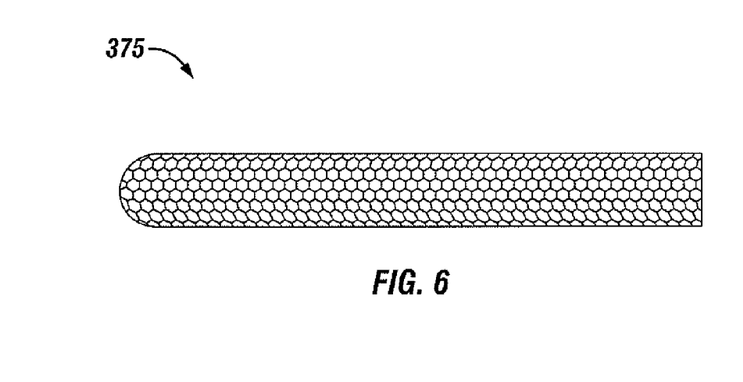

FIGS. 5-6 illustrate an exemplary sequence of chemical reactions for forming the hydrophilic sensing layer 140 and the corresponding hydrophobic reference layer 130, in accordance with the disclosed embodiments. The sensing layer 140 can be made from sulfonated carbon nanotubes (CNT) 350 and the corresponding reference layer 130 can be made from carbon nanotubes 375. The sulfonated carbon nanotube 350 can be obtained by sulfonation of the CNT with sulphuric acid at 300 degrees and placing the sulfonated CNT in dimethylformamide for obtaining a solution of 1% w/w. Such solution can be further sonicated for 6 hours at room temperature in ultrasonical bath. The liquid phase of the CNT based reference layer 130 can be obtained by adding the starting CNT in dimethylformamide solution (1% w/w) and sonification for 6 hours at room temperature in ultrasonical bath.

Figure 7:
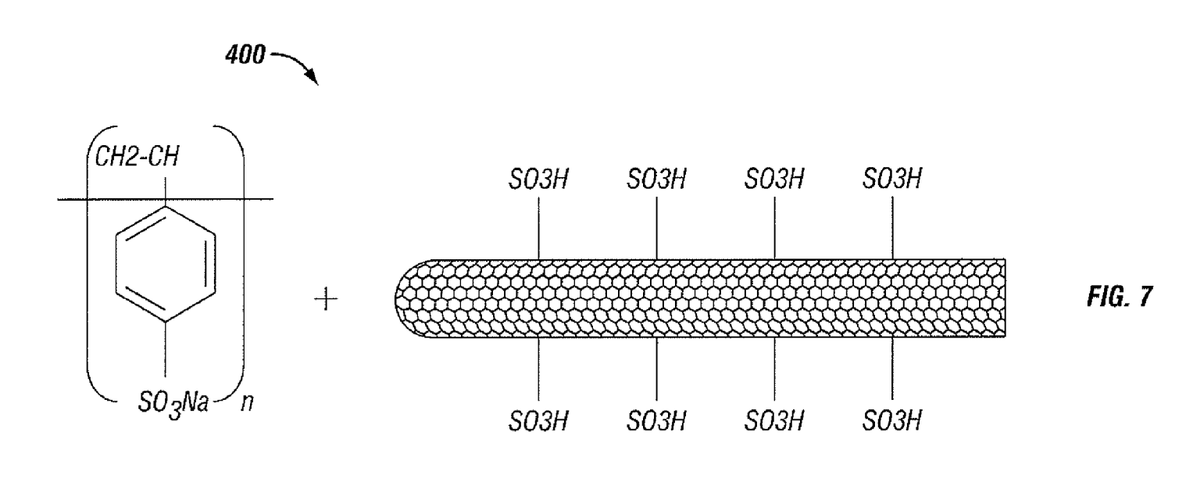
FIGS. 7-8 illustrate an exemplary sequence of chemical reactions for forming the hydrophilic sensing layer and the corresponding hydrophobic reference layer, in accordance with the disclosed embodiments.
Figure 8:
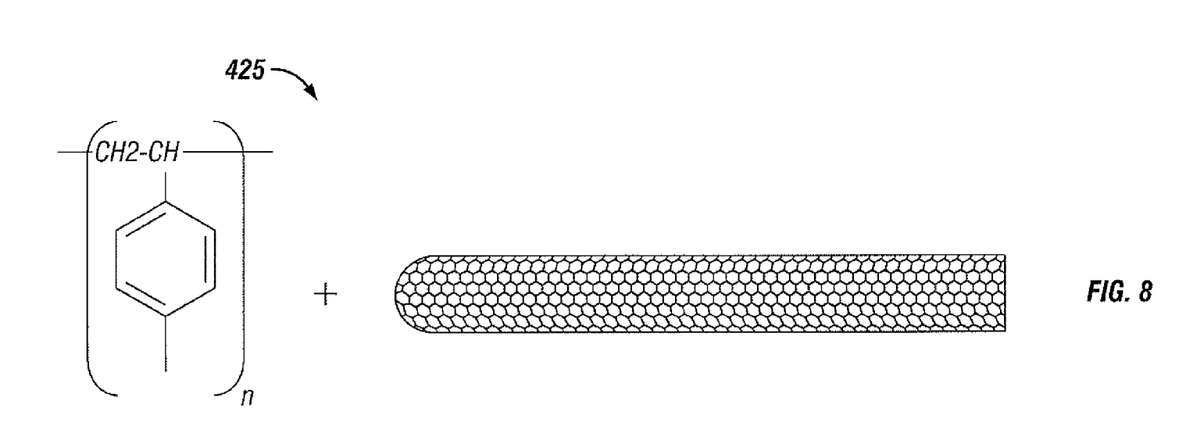

FIGS. 7-8 illustrate an exemplary sequence of chemical reactions for forming the hydrophilic sensing layer 140 and the corresponding hydrophobic reference layer 130, in accordance with the disclosed embodiments. The sensing layer 140 can be configured from a matrix of nano composite of the sulfonated polystyrene and sulfonated CNT 400 and the reference layer 130 can be configured from matrix of polystyrene and CNT 425. The liquid phase of the sensing layer 140 consisting of the matrix nanocomposite of sulfonated polystyrene and sulfonated CNT can be obtained from the above disclosed individual approaches followed by obtaining a solution of 10% w/w poly (sodium p-styrene) sulfonate in dimethylformamide and sulfonated carbon nanotubes in the same solution (1% w/w) is sonicated for 6 hours at room temperature in the ultrasonical bath. The corresponding liquid phase of the matrix nanocomposite reference layer 130 can be obtained from a liquid solution consisting of 10% (w/w) polystyrene in toluene solution and carbon nanotubes (1% w/w) in the same solution is sonicated for 6 hours at room temperature in ultrasonical bath.

Figure 9:
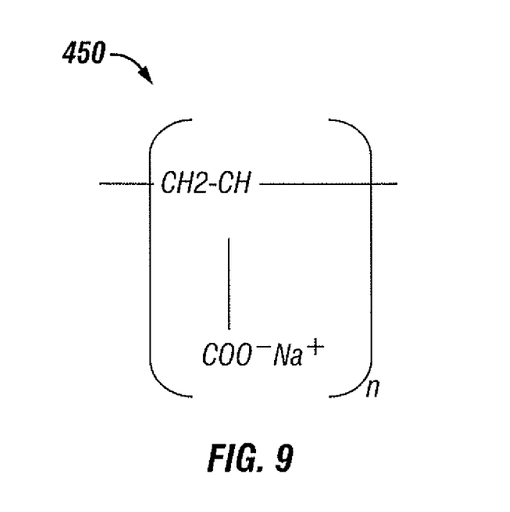
FIGS. 9-10 illustrate an exemplary sequence of chemical reactions for forming the hydrophilic sensing layer and the corresponding hydrophobic reference layer, in accordance with the disclosed embodiments.
Figure 10:
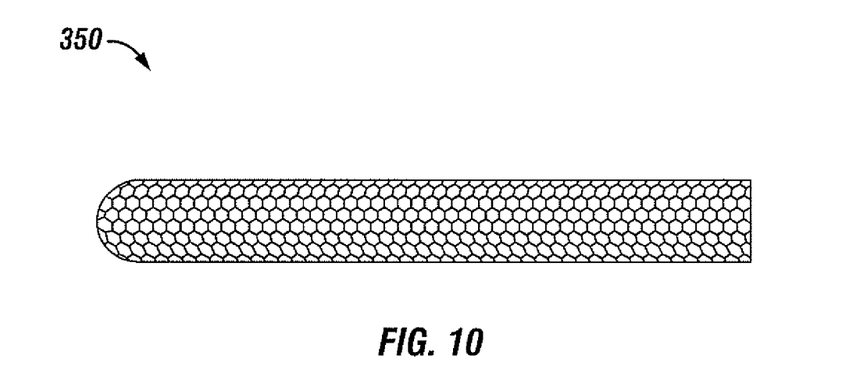
Figure 11:
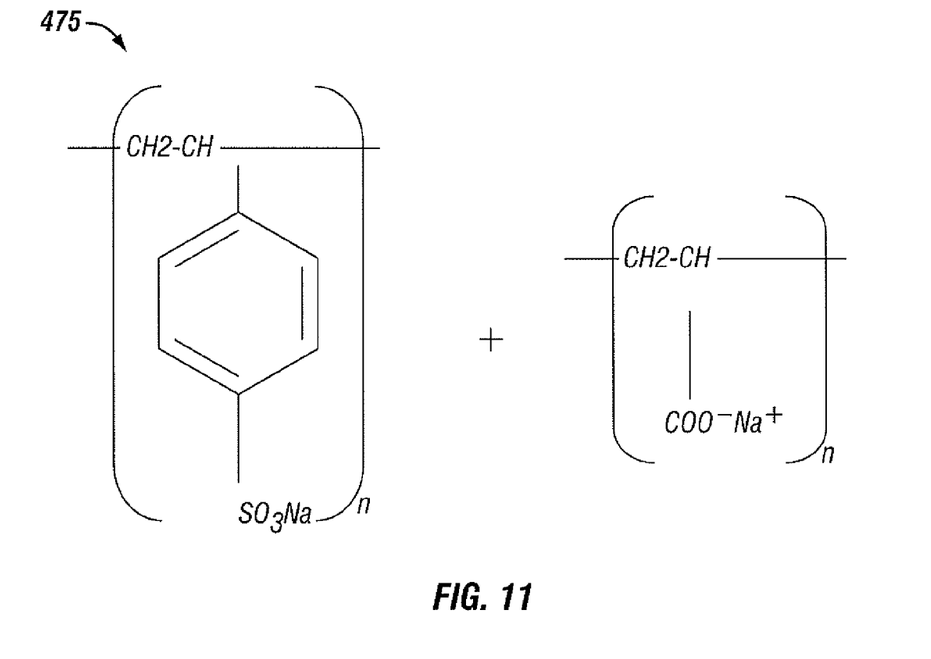
FIGS. 11-12 illustrate an exemplary sequence of chemical reactions for forming the hydrophilic sensing layer and the corresponding hydrophobic reference layer, in accordance with the disclosed embodiments.
Figure 12:
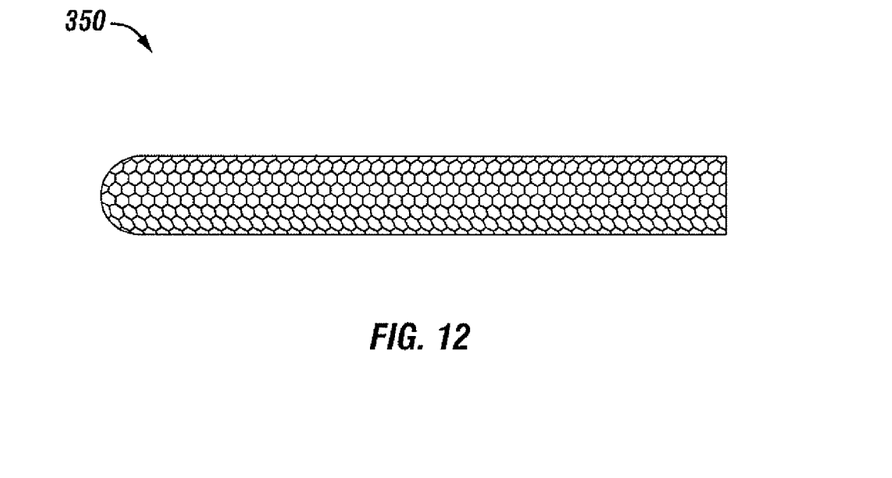
Figure 13:
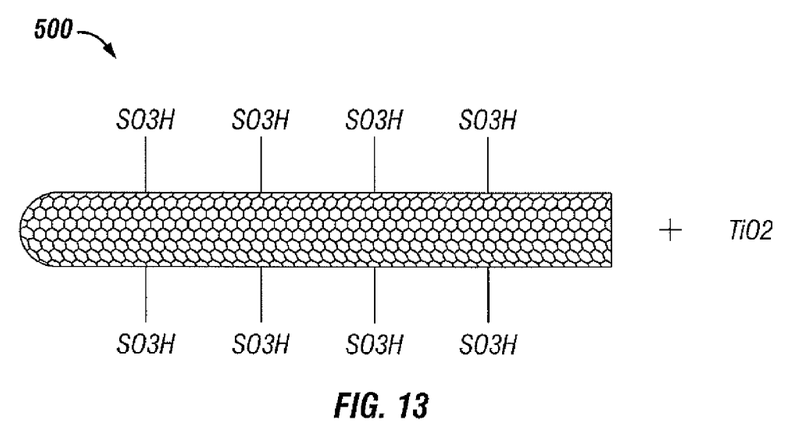
FIGS. 13-14 illustrate an exemplary sequence of chemical reactions for forming the hydrophilic sensing layer and the corresponding hydrophobic reference layer, in accordance with the disclosed embodiments.
Figure 14:
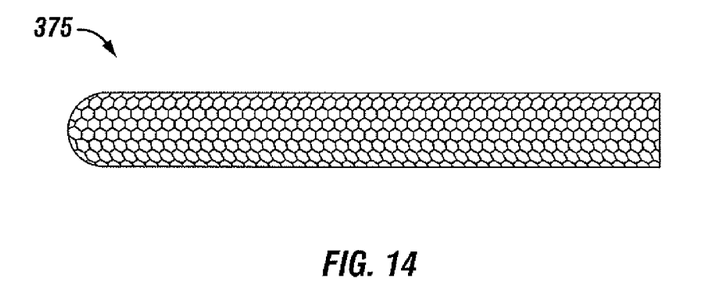

FIGS. 9-10 illustrate an exemplary sequence of chemical reactions for forming the hydrophilic sensing layer 140 and the corresponding hydrophobic reference layer 130, in accordance with the disclosed embodiments. The sensing layer 140 can be obtained by depositing a thin layer of polyacrilic acid 450 as sodium salt onto the CNT 350. The reference layer 130 can be made from the CNT 350. FIGS. 11-12 illustrate an exemplary sequence of chemical reactions for forming the hydrophilic sensing layer 140 and the corresponding hydrophobic reference layer 130, in accordance with the disclosed embodiments. The sensing layer 140 can be a matrix of poly (sodium p-styrene) sulfonate and polyacrilic acid 475 and the reference layer 130 can be made from CNT 350 (with single or double or multi walls). FIGS. 13-14 illustrate an exemplary sequence of chemical reactions for forming the hydrophilic sensing layer 140 and the corresponding hydrophobic reference layer 130 with respect to the vibrating beams 125 and 115, respectively, in accordance with the disclosed embodiments. The sensing layer 140 can be a matrix of nanocomposite based on sulfonated CNT and titania (TiO2) 500 and the reference layer 130 can be made from CNT 375. Note that the CNT 375 shown in FIG. 14 is analogous to the CNT 350 shown in FIG. 12.

Figure 15:
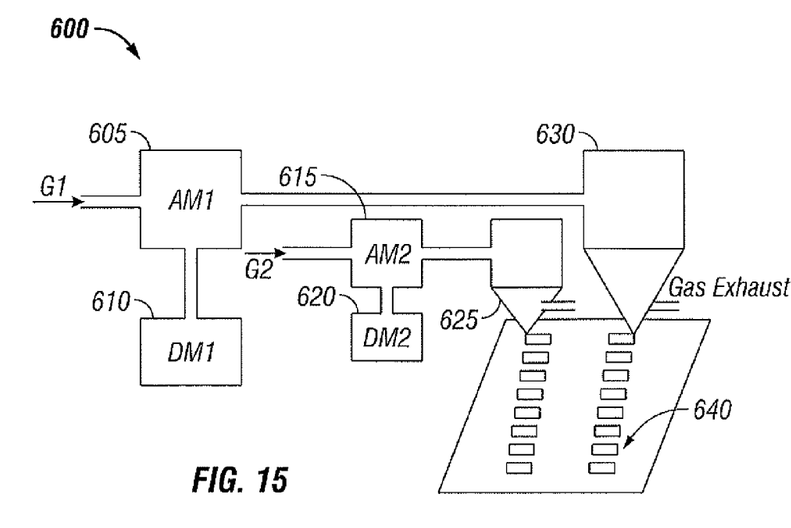
FIG. 15 illustrates a block diagram of a direct printing system for depositing functional layers associated with the differential resonant sensor apparatus on a wafer, in accordance with the disclosed embodiments.

FIG. 15 illustrates a block diagram of an example of direct printing system 600 for depositing functional layers associated with the differential resonant sensor apparatus 100 on a wafer 640 containing a plurality of chips 150, in accordance with the disclosed embodiments, and which may be well suited for the MEMS scale. The deposition of different types of the sensing and reference layer 140 and 130, respectively, on the same chip may be performed by using the additive, selective direct printing system 600. The direct printing system 600 may be employed to deposit the hydrophilic sensing layer 140 liquid solution of the sensing resonant beam 125 on the chip 150 as a part of the wafer 640. Similarly, the hydrophobic reference layer 130 liquid solution of the reference resonant beam 115 can be deposited on the chip 150 of the wafer 640, and repeated on the entire wafer.

The direct printing system 600, for such a dual surface functionalization process generally constitutes a dual-head direct printing system wherein each type of liquid solution utilizes its own distribution system for local, selective and additive deposition with respect to the liquid phase of the particular material. For the case of differential resonant apparatus 100 performed at nano-scale (e.g., NEMS differential chemical resonant sensor), where vibrating beam width is below 0.1 micrometers, other more sophisticated direct printing methods, such as, for example, nano pen lithography, can be utilized in order to assure the positioning accuracy of the functional layer compatible with the beam dimensions.

Below is an example of a direct printing method for the case of the MEMS scale apparatus 100. The homogeneous liquid phase of each solution can be prepared by chemical synthesis. The wafer 640 can be cleaned before liquid phase deposition. An input gas G1 can be passed through a first atomizer module 605. The input gas G1 is further processed by a first deposition material 610 to generate an atomized liquid solution. The atomized liquid solution can be employed to generate multiple reference layers 130 on the wafer 640 through a first nozzle module 630 by additive deposition in the right place on the wafer 640.

Another, input gas G2 can be passed through a second atomizer module 615 to get processed by a second deposition module 620 to generate an atomized liquid solution. The atomized liquid solution can be further employed to generate multiple sensing layers, 140, on the wafer 640 through a second nozzle module 625 by additive deposition in the right place on the wafer 640. Thereafter, the transition from liquid to gel phase of the functionalized layers 140 and 130 can be carried out at the end of deposition of the liquid phase on the surface. The gel layer can then be dried for solvent removal from the gel layer. The gel layer can be thermally consolidated in order to obtain a functionalized thin solid film. The sensing layer 140 and the reference layer 130 can also be prepared on different substrates depending on constrains associated with a chemical functional process. The disclosed differential resonant sensor apparatus 100 containing on-chip sensing and reference layers can therefore provide a genuine relative humidity sensing application, in association with the electronic circuit.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An all-differential resonant sensor apparatus, comprising:
    a sensing loop including a sensing layer deposited on a sensing resonant beam to detect water vapor concentration in an ambient air, wherein said sensing layer is configured from a matrix of nano composite of sulfonated polystyrene and sulfonated carbon nanotubes;
    a reference loop including a reference layer in correspondence with said sensing layer deposited on a reference resonant beam, wherein said reference layer possesses visco-elastic properties identical to that of said sensing loop and wherein said reference layer is configured from a matrix of nano composite of polystyrene and carbon nanotubes; and
    a mixer that detects a difference between a frequency response output from said sensing loop and said reference loop based on absorbed humidity with respect to said sensing resonant beam in order to obtain a drift-free frequency signal.

2. The apparatus of claim 1 wherein said sensing layer comprises a hydrophilic sensing layer for sensing humidity in said ambient air.

3. The apparatus of claim 1 wherein said reference layer comprises a hydrophobic reference layer that does not sense humidity in said ambient air.

4. The apparatus of claim 1 wherein said sensing loop further comprises:
    a sensing electronic circuit interconnected with said sensing resonant beam for signal processing.

5. The apparatus of claim 1 wherein said reference loop further comprises:
    a reference electronic circuit interconnected with said reference resonant beam for signal processing.

6. The apparatus of claim 1 wherein said sensing layer and said reference layer possess identical aging behavior with respect to an external temperature.

7. The apparatus of claim 1 wherein said mixer rejects a common mode signal associated with said sensing loop and said reference loop in order to obtain said drift-free frequency signal.

8. An all-differential resonant sensor apparatus, comprising:
    a sensing loop including a sensing layer deposited on a sensing resonant beam to detect water vapor concentration in an ambient air, wherein said sensing layer comprises a matrix of poly (sodium p-styrenesulfonate) and polyacrilic acid;
    a reference loop including a reference layer in correspondence with said sensing layer deposited on a reference resonant beam, wherein said reference layer possesses visco-elastic properties identical to that of said sensing loop and wherein said reference layer comprises carbon nanotubes;
    a mixer that detects a difference between a frequency response output from said sensing loop and said reference loop based on absorbed humidity with respect to said sensing resonant beam in order to obtain a drift-free frequency signal;
    a sensing electronic circuit interconnected with said sensing resonant beam for signal processing.

9. The apparatus of claim 8 wherein said reference loop further comprises:
    a reference electronic circuit interconnected with said reference resonant beam for signal processing.

10. The apparatus of claim 8 wherein said sensing layer and said reference layer possess identical structural responses and an identical aging behavior with respect to an external temperature.

11. The apparatus of claim 8 wherein said mixer rejects a common mode signal associated with said sensing loop and said reference loop in order to obtain said drift-free frequency signal.

12. An all-differential resonant sensor apparatus, comprising:
    a sensing loop including a sensing layer deposited on a sensing resonant beam to detect water vapor concentration in an ambient air, wherein said sensing layer comprises a nanocomposite of sulfonated carbon nanotubes and titanic;
    a reference loop including a reference layer in correspondence with said sensing layer deposited on a reference resonant beam, wherein said reference layer possesses visco-elastic properties identical to that of said sensing loop and wherein said reference layer comprises carbon nanotubes;
    a mixer that detects a difference between a frequency response output from said sensing loop and said reference loop based on absorbed humidity with respect to said sensing resonant beam in order to obtain a drift-free frequency signal;
    a sensing electronic circuit interconnected with said sensing resonant beam for signal processing.

13. The apparatus of claim 12 wherein said reference loop further comprises:
 a reference electronic circuit interconnected with said reference resonant beam for signal processing.

14. The apparatus of claim 12 wherein said sensing layer and said reference layer possess identical aging behavior with respect to an external temperature.

* * * * *